(12) United States Patent
Narula et al.

(10) Patent No.: US 7,531,489 B2
(45) Date of Patent: May 12, 2009

(54) ORGANOLEPTIC COMPOUNDS AND THEIR USE IN PERFUME COMPOSITIONS

(75) Inventors: Anubhav P. S. Narula, Hazlet, NJ (US); Edward Mark Arruda, Easton, PA (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 12/133,475

(22) Filed: Jun. 5, 2008

(65) Prior Publication Data

US 2008/0242586 A1    Oct. 2, 2008

Related U.S. Application Data

(62) Division of application No. 11/376,385, filed on Mar. 15, 2006, now Pat. No. 7,402,551.

(51) Int. Cl.
  *C11D 3/50* (2006.01)
(52) U.S. Cl. .......................... 510/107; 512/26
(58) Field of Classification Search ............... 510/107; 512/26
  See application file for complete search history.

(56) References Cited

U.S. PATENT DOCUMENTS 3,966,648 A * 6/1976 Schleppnik ............ 512/25

4,125,484 A * 11/1978 Gray et al. ............ 512/14

FOREIGN PATENT DOCUMENTS

EP    1837326    *    9/2007

* cited by examiner

*Primary Examiner*—John R Hardee
(74) *Attorney, Agent, or Firm*—Elizabeth M. Quirk; XuFan Tseng; Joseph F. Leightner

(57) ABSTRACT

The present invention is directed to the novel compounds of the general formula

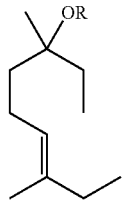

Formula I wherein R represents hydrogen or a straight, branched or cyclic hydrocarbon moiety consisting of less than 15, preferably less than 10, most preferably less than 4 carbon atoms and containing at least one oxygen atom and single and/or double bonds.

6 Claims, No Drawings

ORGANOLEPTIC COMPOUNDS AND THEIR USE IN PERFUME COMPOSITIONS

STATUS OF RELATED APPLICATIONS

This application is a divisional of U.S. Ser. No. 11/376,385, filed Mar. 15, 2006 now issued as U.S. Pat. No. 7,402,551 the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compounds represented by Formula I set forth below:

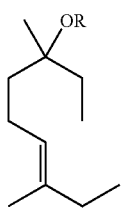

Formula I wherein R represents hydrogen or a straight, branched or cyclic hydrocarbon moiety consisting of less than 15, preferably less than 10, most preferably less than 4 carbon atoms and containing at least one oxygen atom and single and/or double bonds.

In another embodiment, the present invention is directed to the novel compounds represented by the general Formula II set forth below:

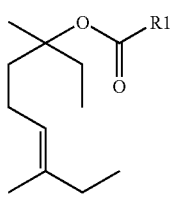

Formula II wherein $R^1$ represents hydrogen or a straight, branched or cyclic hydrocarbon moiety consisting of less than 15, preferably less than 10, most preferably less than 4 carbon atoms and containing single and/or double bonds.

Another embodiment of the invention is directed to a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formulas I and II above, R and $R^1$ independently represent hydrogen or a straight, branched or cyclic hydrocarbon moiety consisting of less than 15, preferably less than 10, most preferably less than 4 carbon atoms and containing single and/or double bonds. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable hydrocarbon moieties containing double bonds include ethene, propene, 1-butene, 2-butene, penta-1-3-deine, hepta-1,3,5-triene and the like. Cyclic hydrocarbons include cyclopropyl, cyclobutyl, cyclohexyl, phenyl and the like.

In another embodiment of the invention, the novel compounds of the invention are represented by the following structures:

Structure I

Structure II

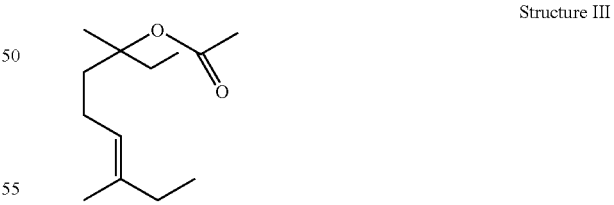

Structure III

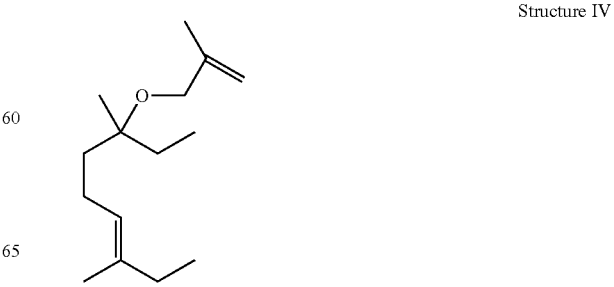

Structure IV

Structure V

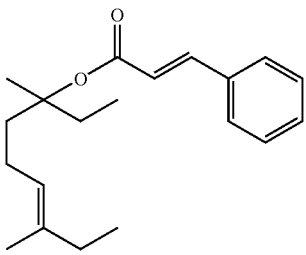

Those with the skill in the art will appreciate that the compound of Structure I is 1,2 Dihydro-Ethyl Linalool; Structure II is 3-Nonene, 7-Methoxy-3,7-Dimethyl; Structure III is 6-Nonen-3-ol 3,7-Dimethyl-Acetate; Structure IV is 3-Nonene, 3,7-Dimethyl-7-[(2-Methyl-2-Propenyl)Oxy]-; and Structure V is 3-phenyl-acrylic acid 1-ethyl-1,5-dimethyl-hept-4-enyl ester.

The compounds of the present invention may be prepared from the corresponding compounds via a catalyzed hydrogenation reaction of the following sequence:

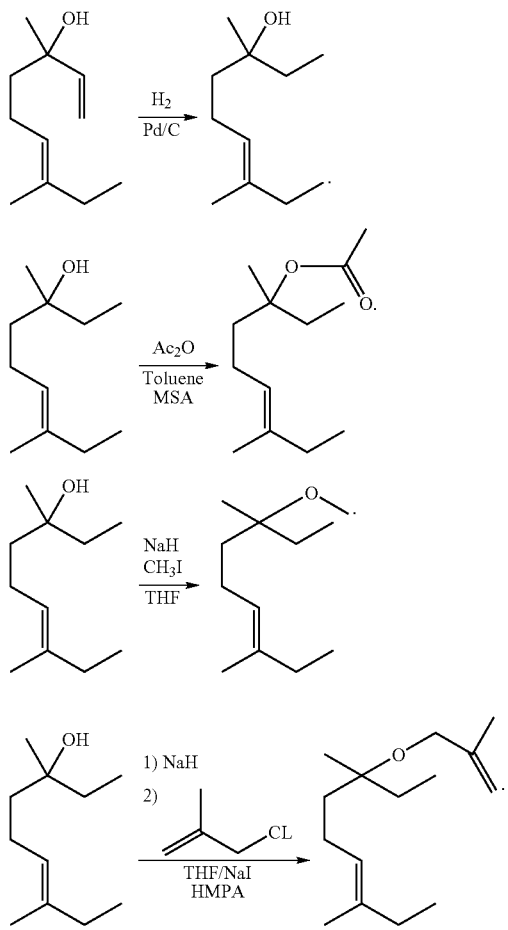

The starting materials for the above reaction are commercially available from Kuraray Chemical Company. Those with skill in the art will appreciate the following catalyst reagents abbreviated as Pd/C is palladium on active carbon, $Ac_2O$ is acetic anhydride, MSA is methanesulfonic acid, NaH is sodium hydride, $CH_3I$ is methyl iodide, THF is tetrahydrofuran and HMPA is hexamethylphosphoric triamide.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

We have discovered that the fragrance compound of Structure I has fresh, floral, muguet, citrus, clean, coriander and bergamot notes. Structure II has strong, linalool, spicy, oregano, green, guava, woody, dihydromyrcenol, citrus, lime and herbal fragrance notes. Structure III has soft, milder, green, dihydromycenol citrus, lime, herbal and woody fragrance notes. Structure IV has strong, cleaner, linalool, less green guava, fruity, dihydromyrcenol citrus, lime and herbal fragrance notes. Structure V has strong, balsamic sweet, floral and spicy fragrance notes.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps,* Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of 6-Nonen-3-ol, 3,7-Dimethyl 1000 g of ethyl linalool (available from Kuraray Chemical Company) and Pd/C were charged in an autoclave. The pressure reservoir was raised to 1720 psi and then the autoclave pressure was held at 100 psi. The reaction was sampled after two hours. The reaction mixture was cooled and allowed to settle. The layers were separated to provide 6-nonen-3-ol, 3,7-dimethyl-.

The NMR of the 6-nonen-3-ol, 3,7-dimethyl- is as follows:
0.9 ppm (s, 3H); 1.0 ppm (s, 3H); 1.2 ppm (s, 3H); 1.4 ppm (m, 4H); 1.6 ppm (m, 2H); 1.7 ppm (s, 2H); 2.0 ppm (m, 3H).

The compound was described to have fresh, floral, muguet, citrus, clean, coriander and bergamot fragrance notes.

EXAMPLE B

Preparation of 3-Nonene, 7-Methoxy-3,7-Dimethyl

To a dry 2 L multi-neck round bottom flask fitted with an air stirrer, nitrogen inlet condenser and an additional funnel, 400 ml of THF, 44 g of NaH, and 21.2 g of dihydroethyl linalool were added and heated to 35-40° C. 170 g of dihydrolinalool g was then added to the reaction mixture dropwise over 2 hours. The mixture was aged for 8 hours. 9 g of HMPA (available from Aldrich Chemical Company) was added and the mixture was stirred. 144 g of $CH_3I$ was added dropwise to the reaction mixture, further aged for two hours and then sampled hourly until maximum conversion was reached. The mixture was cooled and 800 ml of 5% HCl solution was added, allowed to settle, and the organic layer was separated. The aqueous layer was extracted with 3×100 ml of toluene and then dried over $MgSO_4$ to provide 3-nonene, 7-methoxy-3,7-dimethyl-.

The NMR of the 3-nonene, 7-methoxy-3,7-dimethyl- is as follows:
0.9 ppm (m, 3H); 1.3 ppm (s, 6H); 1.4-1.5 ppm (m, 2H); 2.0 ppm (m, 2H); 2.1 ppm (s, 3H); 4.5 ppm (s, 2H); 4.9 ppm (s, 1H); 5 ppm (s, 1H).

The compound was described to have strong, linalool, spicy oregano, green guava, woody, dihydromyrcenol citrus, lime and herbal fragrance notes.

EXAMPLE C

Preparation of 6-Nonen-3-ol, 3,7-Diemthyl-Acetate

To a dry 2 L multi-neck round bottom flask fitted with an air stirrer, nitrogen inlet condenser and an additional funnel, 400 ml of toluene, 0.48 g of MSA and 85 g of dihydroethyl linalool were added and stirred at room temperature. 102 g of acetic anhydride was added dropwise and the temperature was maintained at 30° C. The reaction mixture was sampled hourly until maximum conversion. Water was then slowly added until the acetic anyhydride was decomposed. The contents were washed with cold water, 5% NaOH, and then with brine. The crude was concentrated to give the product.

The NMR of the 6-nonen-3-ol, 3,7-diemthyl-acetate- is as follows:
0.9 ppm (s, 3H); 1.0 ppm (s, 3H); 1.4 ppm (d, 3H); 1.6 ppm (m, 3H); 1.8 ppm (m, 2H); 1.9 ppm (m, 1H); 2.0 ppm (m, 2H).

The compound was described to have soft, milder, green, dihyromycenol citrus, lime, herbal and woody fragrance notes.

EXAMPLE D

Preparation of 3-Nonene, 3,7-Dimethyl-7-[(2-Methyl-2-Propenyl)oxy]

To a dry 2 L multi-neck round bottom flask fitted with an air stirrer, nitrogen inlet condenser and an additional funnel, 200 ml of THF, 50 g of sodium hydride and 300 ml of THF were added and stirred. The mixture was then heated to reflux. 170 g of dihydroethyl linalool was added dropwise over a 1 hour period. The mixture was then aged for 8 hours. 5 g of NaI and 9 g of hexamethylphosphoramide (HMPA) were added to the mixture and heating was resumed. 110 g of methallyl chloride was added dropwise to the mixture. The product was isolated after usual work up.

The NMR of the 3-nonene, 3,7-dimethyl-7-[(2-methyl-2-propenyl)oxy]- is as follows:
0.9 ppm (s, 3H); 1.0 ppm (s, 3H); 1.1 ppm (s, 3H); 2.0 ppm (m, 4H); 3.7 ppm (s, 2H); 4.8 ppm (s, 1H); 5.0 ppm (s, 2H); 5.1(m, 1H).

The compound was described to have strong, cleaner, linalool, less green guava, fruity, dihydromyrcenol citrus, lime and herbal fragrance notes.

EXAMPLE E

Demonstration Fragrance Formula with Ethyl Dihydrolinalool

| DESCRIPTION | PARTS |
|---|---|
| BACDANOL BHT | 1.00 |
| ETHYL DIHYDROLINALOOL | 10.00 |

-continued

| DESCRIPTION | PARTS |
|---|---|
| ALD AA TRIPLAL BHT 10% DEP | 0.50 |
| ALD C-11 ULENIC UB BHA 10% DEP | 0.20 |
| MENTHOL CRYST USP NAT | 0.50 |
| CYCLOGALBANIFF BHT 10% DEP | 0.50 |
| METH SALICYLATE | 0.10 |
| BENZYL ACETATE | 5.00 |
| BENZYL SALICYLATE | 4.00 |
| CINN ALCOHOL | 2.00 |
| GALAXOLIDE 50 PCT DEP | 6.00 |
| HELIOTROPINE (PIPERONAL) (USDEA) | 5.00 |
| PHEN ETH ALC WHITE EXTRA | 10.00 |
| SANDALWOOD OIL INDIA RECT LMR | 2.00 |
| SANTALIFF BHT | 5.00 |
| VERTOFIX COEUR | 2.00 |
| ACALEA BHT/BHA | 2.00 |
| HYDROXYCIT EXTRA | 3.00 |
| LILIAL | 4.00 |
| LYRAL BHT | 7.00 |
| VANILLIN EX LIGNIN | 2.00 |
| DIPROPYLENE GLYCOL | 26.20 |
| ISO E SUPER BHT | 2.00 |
| TOTAL: | 100.00 |

The ethyl dihydrolinalool provided a more floral and more diffusive note to the fragrance formulation.

What is claimed is:

1. A method of improving, enhancing or modifying a fragrance formulation through the addition of an olfactory acceptable amount of the compound of formula wherein $R^1$ represents hydrogen or a straight, branched or cyclic hydrocarbon moiety consisting of less than 15 carbon atoms and containing single and/or double bonds.

2. The method of claim 1, wherein the fragrance formulation is incorporated into a product selected from the group consisting of a perfume, a cologne, toilet water, a cosmetic product, a personal care product, a fabric care product, a cleaning product, and an air freshener.

3. The method of claim 2, wherein the cleaning product is selected from the group consisting of a detergent, a dishwashing composition, a scrubbing compound, and a window cleaner.

4. The method of claim 1, wherein the olfactory acceptable amount is from about 0.005 to about 10 weight percent.

5. The method of claim 4, wherein the olfactory acceptable amount is from about 0.5 to about 8 weight percent.

6. The method of claim 1, wherein the olfactory acceptable amount is from about 1 to about 7 weight percent.

* * * * *